United States Patent [19]

Tennant

[11] 4,254,509
[45] Mar. 10, 1981

[54] ACCOMMODATING INTRAOCULAR IMPLANT

[76] Inventor: Jerald L. Tennant, 806 Greentree Ct., Duncanville, Tex. 75116

[21] Appl. No.: 28,609

[22] Filed: Apr. 9, 1979

[51] Int. Cl.³ .............................................. A61F 1/16
[52] U.S. Cl. ......................................................... 3/13
[58] Field of Search ............................................... 3/13

[56] References Cited

U.S. PATENT DOCUMENTS

| 2,834,023 | 5/1958 | Lieb | 3/13 |
| 3,961,379 | 6/1976 | Highgate | 3/13 |
| 3,992,563 | 11/1976 | Tanaka | 3/13 X |

FOREIGN PATENT DOCUMENTS 1034325  7/1958  Fed. Rep. of Germany ................. 3/13

OTHER PUBLICATIONS

Tennant, *A Lens For All Seasons*, Copyright 1976, (Book).

*Primary Examiner*—Clifford D. Crowder

[57] ABSTRACT

An eye implant has an optical lens anteriorly convex and posteriorly planar supported on two diametrically opposed coplanar feet through two supporting members forming an arch. Each supporting member is unitary with the lens and rooted in one of the feet outside the perimeter of the lens to support the lens with the posterior thereof anterior to the plane of the feet. The lens is formed of a rigid biologically inert material. The supporting members are formed of soft biologically supporting material. The resulting structure, when fixed into the sclera of the eye, will change as to move the lens anteriorly when forces are applied to the feet upon contraction of the ciliary body.

4 Claims, 6 Drawing Figures

ACCOMMODATING INTRAOCULAR IMPLANT

TECHNICAL FIELD

This invention relates to intraocular lenses and more particularly to an accommodating intraocular lens.

BACKGROUND ART

Over the past two decades, operation techniques and lens structures have been developed which, when suitably handled, restore vision to eyes blinded by cataracts. In general, the development of such lenses and the surgical techniques involved in connection with such lenses are described in Applicant's book entitled *A Lens for All Seasons*, Tennant, Dallas, Tex. 1976. Such lenses have been extensively used with great success. Briefly described, Applicant's prior lens system as set forth in the above publication is a unitary structure having an optical lens anteriorly convex and posteriorly planar with two diametrically opposed pairs of coplanar feet extending away from the lens. Two supporting members forming an arch are included in the unitary structure and couple the lens to the feet outside the perimeter of the lens and support the lens with the posterior thereof anterior to the plane of the feet.

There exists a need for structure which more closely conforms with the action of the natural eye, particularly as to the phenomena of accommodation. Prior intraocular lenses have not provided for accommodation, and it is to this aspect of intraocular implant lenses that the present invention is directed.

DISCLOSURE OF THE INVENTION

In accordance with the present invention, an intraocular lens structure is provided which permits accommodation. Thus, in a lens structure having coplanar oppositely directed pairs of feet integrally formed with arched haptics for the support of the lens anterior to the transiridial plane. The present invention involvves a lens having at the haptic portion of the structure a soft material as to be responsive to shape changing forces upon contraction of the ciliary body, increasing the iris-lens spacing and moving the image forward. Further, soft feet may be provided for achieving more gentle interaction between the feet and the scleral spur. In another aspect, the present invention involves an accommodating intraocular lens structure, wherein a rigid lens portion is provided of methylmethacrylate-like material having a posteriorly plano-anteriorly convex configuration. Arched haptics support the lens portion while being integrated in a unitary structure with coplanar oppositely directed feet where at least a portion of the haptics are of soft material, permitting increase in spacing of the lens from the transiridial plane upon contraction of the ciliary muscles.

BRIEF DESCRIPTION OF THE DRAWINGS

A more complete understanding of the invention may be had by referring to the following detailed description when taken in conjunction with the drawings, wherein.

DETAILED DESCRIPTION

Figure 1:
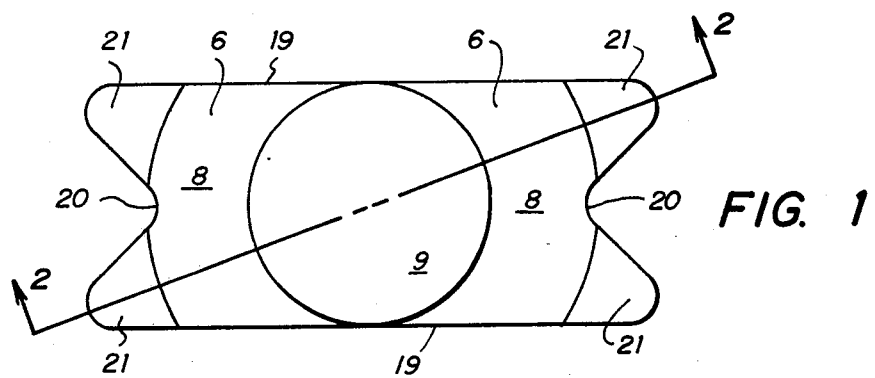
FIG. 1 is a top view of a lens embodying the present invention.

FIGS. 1-5 illustrate an artificial lens adapted to fixate in the scleral spur of the eye while positioned in the anterior chamber. The structure comprises an optical lens section 9 and supporting structure 6.

The lens 9 is formed of materials which are biologically inert, i.e., not susceptible to being absorbed by the body fluids and capable of being well tolerated by the human body when implanted. Exemplary of rigid materials is polymethyl methacrylate, hereinafter referred to as PMMA. Representative of soft materials are soft hydrogels of hydrophilic type such as 2-hydroxyethyl methacrylate, generally referred to as PHEMA. By the following formula, one suitable PHEMA compound is specifically identified:

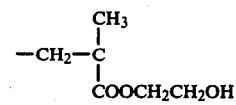

The anterior surface 10 of lens 9 is convex. The posterior surface 11 is planar. The thickness of the lens 9 along the optical axis 14 (FIG. 5) is variable depending upon the power of the lens.

The artificial lens structure comprising an optical lens portion 9 and supporting structure 6 is preferably manufactured as an integral unit, but with different parts thereof of materials of different compositions. The supporting structure 6 comprises arches 8 terminating in feet 7. Arches 8 are integral with the lens 9 and with feet 7.

Arches 8 are in the form of a medial slice out of an inverted disk which has a flat bottom. In such structure, the parallel sides 19 are tangent to the circumference of the lens 9.

Each foot 7 has two toes 21 forming a chordioid like edge 20 shaped to hold the supporting structure 6 in situ in the anterior chamber of the eye. The sides of foot 7 are parallel to the longitudinal axis of the structure and along the outside of each toe 21 are rectilinear.

In accordance with one embodiment of this invention, lens section 9 is made of material such as PMMA, while the haptics or arches 8 are made of soft material such as PHEMA. With such construction the haptics 8 may be made to undergo beam bending in response to forces produced by muscles in the eye, specifically to move the lens section 9 forward.

Both the haptics 8 and feet 7 may be made of PHEMA material to provide accommodation. In all cases, soft material is employed to permit change in the relationships between the lens section 9 and feet 7 when forces produced present in the eye are encountered. This permits accommodation in a somewhat natural involuntary manner.

Figure 6:
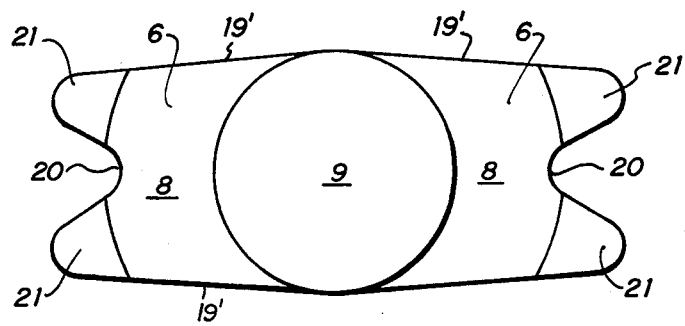
FIG. 6 is a top view of a modification of the invention.

The lens in FIG. 6 is much the same configuration as the lens of FIGS. 1-5 except that the sides 19', though tangent to lens 9, are nonparallel, angled inward in the direction of feet 7.

Figure 2:
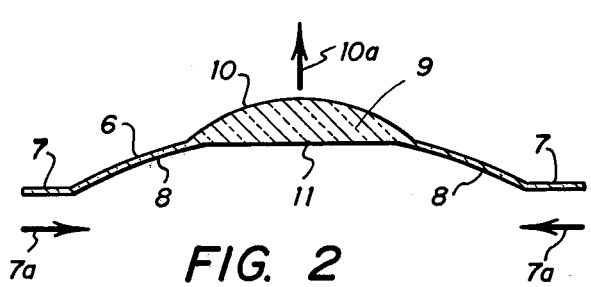
FIG. 2 is a cross-sectional view taken along line 2—2 of FIG. 1.

In FIG. 2 the optical lens 9 shape in its preferred embodiment is shown wherein the anterior surface 10 is convex and the posterior surface 11 is planar and supported by arches 8 from feet 7 as to be clear of the iris, thereby avoiding problems attendant to the irritation resulting from operative procedures during removal of the natural lens and the implant thereof.

Exemplary dimensional parameters of the particular embodiment of the invention described in FIGS. 1 through 5 are:

diameter of lens 9=6.0 mm.;
lateral dimension of foot 7=5.0 mm.;
thickness of lens 9 along the optical axis 14, variable according to the power of the lens;
thickness of foot 7 perpendicular to the ciliary area=0.25 mm.;
distance from toe to toe=11.0 mm. to 14.0 mm. in 0.5 mm. steps.

The distance from the transiridial plane to the lens posterior along the optical axis 14 preferably is about ¾ mm.

Figure 3:
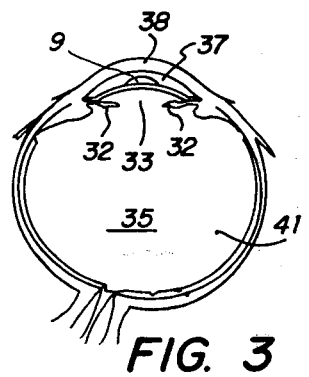
FIG. 3 is a cross-sectional view of the eye showing the lens in situ.
Figure 4:
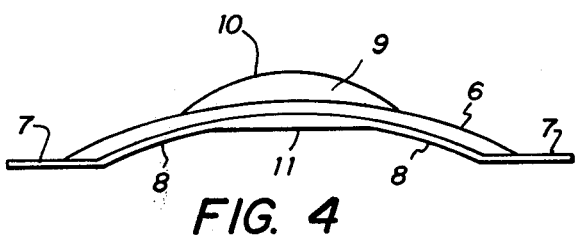
FIG. 4 is a side elevational view of the lens of FIGS. 1-3.
Figure 5:
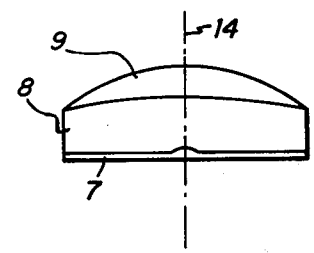
FIG. 5 is an end view of the lens of FIGS. 1-4.

In FIG. 3, the lens 9 is illustrated as inserted into an eye 41. Posterior chamber 35 is separated from anterior chamber 37 by the iris 32. The iris 32 is comprised of spongy tissue and has a central aperture or pupil 33. The cornea 38 defines the outside boundary of the anterior chamber 37. During surgical implantation of the intraocular lens, an incision is made in the cornea 38, and the cornea 38 is carefully lifted away to permit surgical entry into the eye 41. After the natural lens is removed, the lens structure is then positioned in the anterior chamber of the eye anterior to the iris 32.

The intraocular lens 9 functions to provide accommodation by supporting the optical structure anterior to the iris and movably holding the lens in front of the pupillary aperture by means of the supporting structure which extends to the boundary of the anterior chamber and responds to lateral forces on the feet 7 to change the lens-retina spacing. More particularly, if forces are applied in the direction of arrows 7a, FIG. 2, then with the implant totally or partly of soft materials, the lens will be moved in direction 10a thereby changing the optics in the eye. In effect, the lens section is coupled to the feet by a structural hinge which permits change in the angle between the posterior plane of the lens and the structure forming the haptics and feet. The haptics and feet are proportioned and of such material that the haptics may be distorted without distortion of the lens section and such that the position of the lens section may be forced to change. The effect will be to move the image forward, and thus, in a manner which generally corresponds to that of the natural eye, provides for focusing onto the retina of objects at varying distances from the eye. It is noted that the chemistry of PMMA and PHEMA materials is well known. Extensive study of such materials has been undertaken in connection with developments relating to contact lenses. Three manuscripts contained in Montague Ruben's *Soft Contact Lenses*, John Wiley & Sons, 1978, New York, which extensively treat the subject of the materials here involved are:

1. "The Beginning of the Soft Lens", Otto Wichterle, pp. 3-5.
2. "The Development of pHEMA for Contact Lens Wear", Maximilian Dreifus, pp. 7-15.
3. "The Chemistry of Soft Hydrogel Lens Materials", Miguel F. Refojo, pp. 19-38.

Although particular embodiments of the invention have been illustrated in the drawings and described herein, it will be understood that the invention is not limited to the embodiments disclosed, but is capable of rearrangement, modification and substitution of parts and elements without departing from the spirit of the invention.

I claim:

1. In an eye implant having an optical lens anteriorly convex and posteriorly planar supported on two diametrically opposed coplanar feet through two supporting members forming a substantially continuous arched surface, each supporting member being unitary with said lens and rooted in one of said feet outside the perimeter of said lens and supporting said lens with the posterior thereof anterior to the plane of said feet, the improvement comprising said lens being formed of a rigidly biologically inert material, and said supporting members being formed of soft biologically supporting hydrogel material to provide structure which, when fixed into the eye, moves said lens anteriorly only along the axis of the eye when forces are applied to said feet upon contraction of the ciliary body.

2. The implant of claim 1, said lens being formed of material such as polymethyl methacrylate and said supporting members being formed of material such as PHEMA.

3. An accommodating artificial implant lens to be fixed into an eye which comprises:
   (a) a substantially continuous arched surface structural support of soft biologically inert hydrogel lens material,
   (b) coplanar oppositely directed feet extending from opposite ends of said support, of dimension to extend to the boundary of the anterior chamber of the eye, and shaped to fix the position thereof into the eye, and
   (c) a lens formed in said structural support anteriorly convex and posteriorly shaped for substantial clearance above the plane of said feet and of hard biologically inert lens material and movable only away from the iris of the eye along the axis of the eye upon bending of said support in response to contraction of the ciliary body.

4. The combination set forth in claim 3 in which said structural support is formed of PHEMA compounds and said lens is formed of material such as polymethyl methacrylate.

* * * * *